(12) United States Patent
Sato et al.

(10) Patent No.: US 9,538,977 B2
(45) Date of Patent: Jan. 10, 2017

(54) X-RAY DIAGNOSIS APPARATUS AND DOSE DISTRIBUTION DATA GENERATION METHOD

(71) Applicant: TOSHIBA MEDICAL SYSTEMS CORPORATION, Otawara-Shi (JP)

(72) Inventors: Naotaka Sato, Otawara (JP); Shingo Abe, Nasushiobara (JP); Katsuie Ikawa, Nasushiobara (JP); Masahiro Ozawa, Sakura (JP); Yusuke Kanno, Otawara (JP); Jun Sakakibara, Otawara (JP); Satoshi Yamashita, Utsunomiya (JP); Yuichiro Watanabe, Yaita (JP)

(73) Assignee: TOSHIBA MEDICAL SYSTEMS CORPORATION, Otawara-Shi (JP)

(*) Notice: Subject to any disclaimer, the term of this patent is extended or adjusted under 35 U.S.C. 154(b) by 147 days.

(21) Appl. No.: 14/119,381

(22) PCT Filed: Oct. 2, 2012

(86) PCT No.: PCT/JP2012/075492
§ 371 (c)(1),
(2) Date: Nov. 21, 2013

(87) PCT Pub. No.: WO2013/051550
PCT Pub. Date: Apr. 11, 2013

(65) Prior Publication Data
US 2014/0146944 A1 May 29, 2014

(30) Foreign Application Priority Data
Oct. 7, 2011 (JP) .................................. 2011-222639

(51) Int. Cl.
*H05G 1/42* (2006.01)
*A61B 6/00* (2006.01)

(52) U.S. Cl.
CPC .............. *A61B 6/542* (2013.01); *A61B 6/4233* (2013.01); *A61B 6/4441* (2013.01); *A61B 6/481* (2013.01); *A61B 6/504* (2013.01)

(58) Field of Classification Search
CPC .......... A61B 5/065; A61B 6/485; G03B 42/02
(Continued)

(56) References Cited

U.S. PATENT DOCUMENTS 5,548,627 A * 8/1996 Swerdloff et al. ................. 378/4
6,422,751 B1 7/2002 Aufrichtig et al.
(Continued)

FOREIGN PATENT DOCUMENTS

CN 1747688 A 3/2006
JP 64-54341 A 3/1989
(Continued)

OTHER PUBLICATIONS

International Search Report Issued Nov. 13, 2012 in PCT/JP12/075492 Filed Oct. 2, 2012.
(Continued)

Primary Examiner — Jason McCormack
(74) Attorney, Agent, or Firm — Oblon, McClelland, Maier & Neustadt, L.L.P.

(57) ABSTRACT

An X-ray diagnosis apparatus detects X-rays output from an X-ray source and transmitted through a subject, and generates images of the inside of the subject, and comprises a detector, an X-ray intensity distribution data generator, and an entrance dose distribution data generator. The detector detects the intensity of the X-rays output from the X-ray source. The X-ray intensity distribution data generator generates X-ray intensity distribution data showing the X-ray intensity for each of a plurality of subdomains of an X-ray irradiation field from the X-ray source based on the detection outcome by the detector. The entrance dose distribution
(Continued)

data generator generates entrance dose distribution data showing the dose of X-rays output from the X-ray source and irradiated onto the subject, based on the X-ray intensity distribution data.

8 Claims, 12 Drawing Sheets

(58) Field of Classification Search
USPC .................. 378/147, 98.7, 207, 116, 19
See application file for complete search history.

(56) References Cited

U.S. PATENT DOCUMENTS

| | | | | |
|---|---|---|---|---|
| 6,713,773 | B1* | 3/2004 | Lyons | A23L 3/263 250/453.11 |
| 2003/0095625 | A1* | 5/2003 | Steinberg | A61N 5/1048 378/65 |
| 2004/0028182 | A1* | 2/2004 | Tamegai | A61B 6/00 378/98.7 |
| 2006/0056592 | A1 | 3/2006 | Tamegai | |
| 2006/0104420 | A1 | 5/2006 | Mollus | |
| 2006/0256915 | A1* | 11/2006 | Otto | A61N 5/1031 378/65 |
| 2010/0086104 | A1* | 4/2010 | Michaelsen et al. | 378/71 |

FOREIGN PATENT DOCUMENTS

| | | |
|---|---|---|
| JP | 2000 65943 | 3/2000 |
| JP | 2004 69441 | 3/2004 |
| JP | 2005 198762 | 7/2005 |
| JP | 2006 223 | 1/2006 |
| JP | 2007 215918 | 8/2007 |
| JP | 2008 104704 | 5/2008 |
| JP | 2008 132147 | 6/2008 |
| JP | 2008-142390 A | 6/2008 |
| JP | 2008 200323 | 9/2008 |

OTHER PUBLICATIONS

Combined Office Action and Search Report issued Apr. 13, 2015 in Chinese Patent Application No. 201280035012.7 (with English translation of categories of cited documents).

* cited by examiner

|   | a | b | c | d | e |
|---|---|---|---|---|---|
| 1 | 90 | 100 | 110 | 100 | 100 |
| 2 | 65 | 100 | 125 | 110 | 100 |
| 3 | 60 | 110 | 120 | 110 | 100 |
| 4 | 60 | 110 | 120 | 110 | 100 |
| 5 | 100 | 100 | 110 | 100 | 90 |

FIG. 4B

| 223 | a | b | c | d | e |
|---|---|---|---|---|---|
| 1 | 100 | 100 | 100 | 50 | 50 |
| 2 | 100 | 100 | 100 | 50 | 50 |
| 3 | 100 | 100 | 100 | 50 | 50 |
| 4 | 100 | 100 | 100 | 50 | 50 |
| 5 | 100 | 100 | 100 | 50 | 50 |

| 223 | a | b | c | d | e |
|---|---|---|---|---|---|
| 1 | 125 | 125 | 125 | 62.5 | 62.5 |
| 2 | 125 | 125 | 125 | 62.5 | 62.5 |
| 3 | 125 | 125 | 125 | 62.5 | 62.5 |
| 4 | 125 | 125 | 125 | 62.5 | 62.5 |
| 5 | 125 | 125 | 125 | 62.5 | 62.5 |

|   | a | b | c | d | e |
|---|---|---|---|---|---|
| 1 | 112.5 | 125 | 137.5 | 62.5 | 62.5 |
| 2 | 81.3 | 125 | 156.3 | 68.8 | 62.5 |
| 3 | 75 | 137.5 | 150 | 68.8 | 62.5 |
| 4 | 75 | 137.5 | 150 | 68.8 | 62.5 |
| 5 | 125 | 125 | 137.5 | 62.5 | 56.3 |

M2 (columns d, e)

FIG. 5B
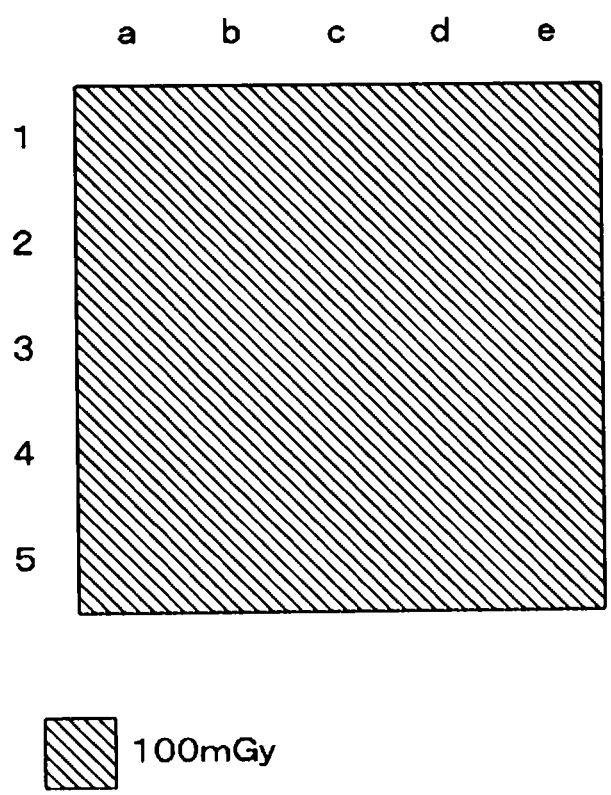
 100mGy

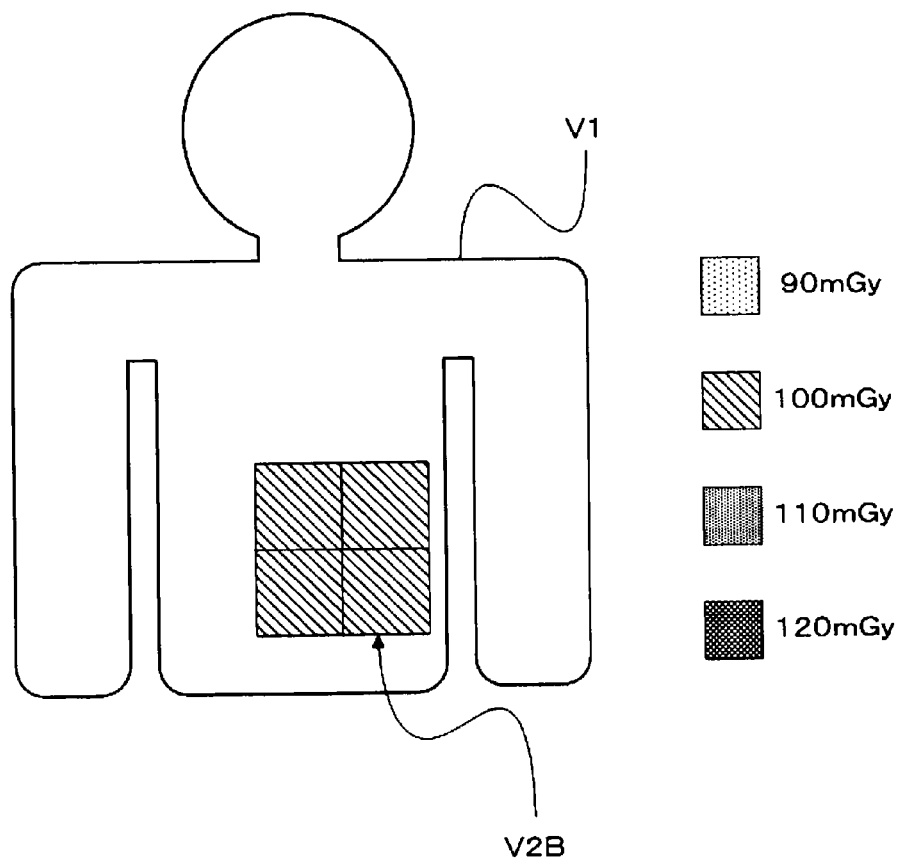

US 9,538,977 B2

X-RAY DIAGNOSIS APPARATUS AND DOSE DISTRIBUTION DATA GENERATION METHOD

TECHNICAL FIELD

The embodiment of the present invention relates to an X-ray diagnosis apparatus and the technique of a dose management method.

BACKGROUND ART

The X-ray diagnosis apparatus irradiates X-rays from an X-ray tube onto a patient, captures the X-rays transmitted through the subject using an X-ray detector, and the like, and generates a fluoroscopic image or a captured image, which is a shadowgram proportionate to the transit dose thereof. Subsequently, operators, including doctors, laboratory personnel, and the like (hereinafter, simply referred to as "operator") observe the fluoroscopic image or captured image generated by the X-ray diagnosis apparatus, thereby diagnosing the subject.

Managing the dose irradiated onto the subject becomes very important upon diagnosis using the X-ray diagnosis apparatus above. This is because when the entrance dose is high, there is a danger of irradiation damage being caused to the body tissue.

Meanwhile, there is a case such that the intensity distribution of the X-rays being irradiated from the X-ray tube varies depending on the configuration of the X-ray diagnosis apparatus and conditions upon photographing. For example, there is a case such that when electron beams collide with an anode within the X-ray tube and X-rays are generated, the intensity distribution of the generated X-rays becomes varied due to a heel effect. Moreover, there is a case such that, depending on the collimator and conditions of the filter, the intensity of the X-ray transmitting a part of the irradiation field decreases. Furthermore, when a top is interposed between the X-ray tube and the subject, some X-rays are absorbed by the top at a part where the top is interposed, causing the intensity of the X-rays of the part to decrease.

PRIOR ART DOCUMENT

Patent Document

[Patent Document 1] Japanese Unexamined Patent Application Publication No. 2005-198762

SUMMARY OF THE INVENTION

Problems to be Solved by the Invention

The problem to be solved by the present invention is to allow management of the entrance dose for each specified domain within an irradiation field even under circumstances when variance is generated in the intensity distribution of X-rays within the irradiation field.

Means of Solving the Problems

In order to achieve the abovementioned purpose, a first embodiment 1 of the present embodiment is an X-ray diagnosis apparatus that detects X-rays output from a X-ray source and transmitted through a subject and generates images of the inside of the subject, and comprises a detector, an X-ray intensity distribution data generator, and an entrance dose distribution data generator. The detector detects the intensity of the X-rays output from the X-ray source. The X-ray intensity distribution data generator generates X-ray intensity distribution data showing the X-ray intensity for each of a plurality of subdomains of an X-ray irradiation field from the X-ray source, based on the detection outcome by the detector. The entrance dose distribution data generator generates entrance dose distribution data showing the dose of X-rays, which are output from the X-ray source and irradiated onto the subject, based on the X-ray intensity distribution data.

BRIEF DESCRIPTION OF THE DRAWINGS

FIG. 4B is a figure describing a relation between a compensating filter and the entrance dose.

FIG. 4C is a figure describing a relation between the compensating filter and the entrance dose.

FIG. 4D is a figure describing a relation between the compensating filter and the entrance dose.

FIG. 5B illustrates an example of the method for managing the entrance dose.

FIG. 6B is an example of the display modes of the information indicating the entrance dose.

MODES FOR CARRYING OUT THE INVENTION

Figure 1:
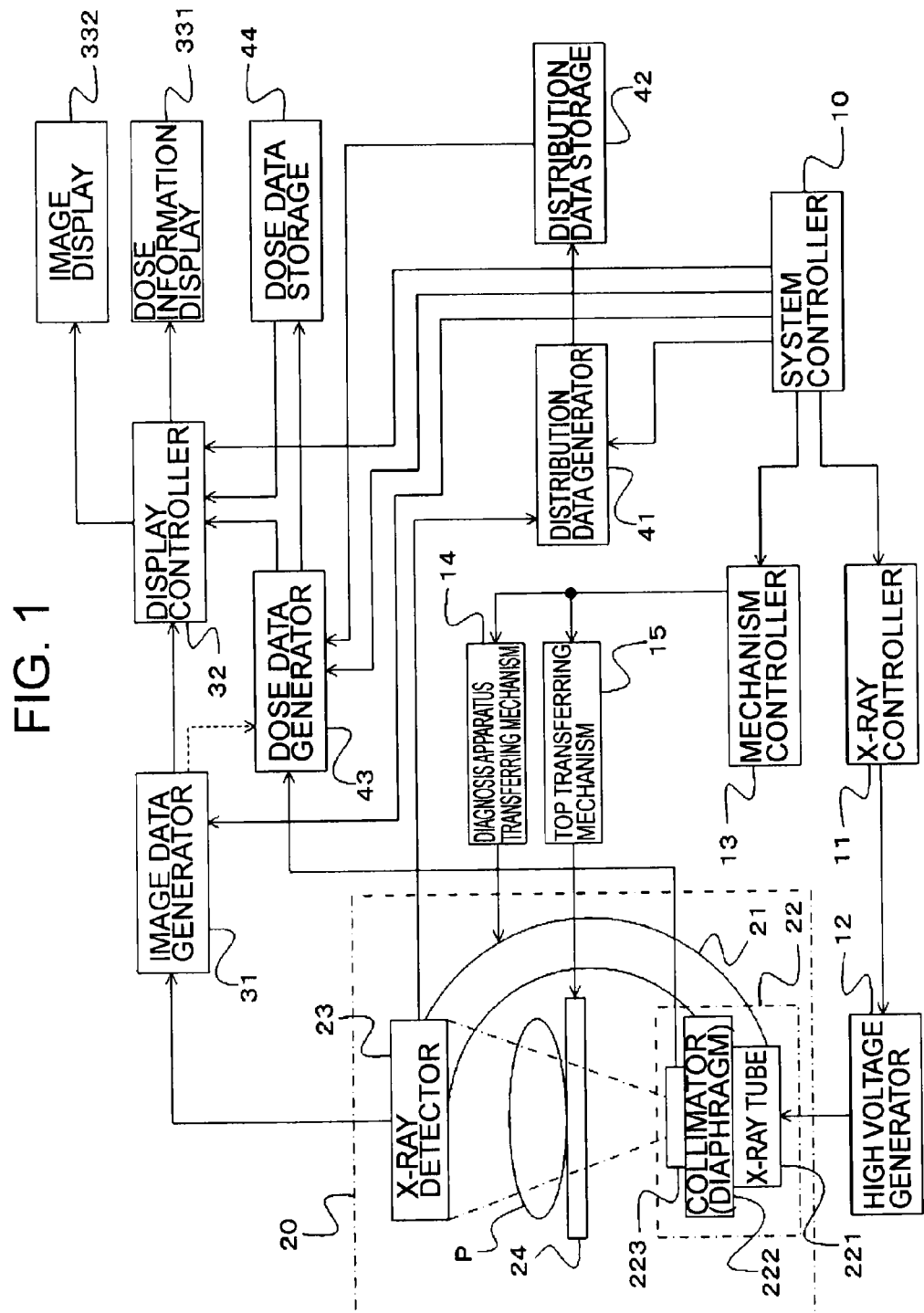
FIG. 1 is a block diagram of an X-ray diagnosis apparatus related to the present embodiment.

A medical image processing apparatus related to the present embodiment is described with reference to FIG. 1. As illustrated in FIG. 1, the X-ray diagnosis apparatus related to the embodiment comprises a capturing unit 20, a system controller 10, an X-ray controller 11, a high voltage generator 12, a mechanism controller 13, a diagnosis apparatus transferring mechanism 14, a top transferring mechanism 15, an image data generator 31, a display controller 32, a dose information display 331, an image display 332, a distribution data generator 41, a distribution data storage 42, a dose data generator 43, and a dose data storage 44.

In addition, the capturing unit 20 comprises a C arm 21, an X-ray generator 22, an X-ray detector 23, and a top 24. The C arm 21 is a retaining part that retains the X-ray generator 22 and the X-ray detector 23. The X-ray generator 22 is retained on one end of the C arm 21. The X-ray detector 23 is retained on the other end of the C arm 21 such that the detector 23 faces the X-ray generator 22. For example, the C arm 21 is rotatably supported by an arc-like pillar hung from a ceiling. The top 24 of a couch placed on a subject P is arranged between the X-ray generator 22 and the X-ray detector 23. The X-ray generator 22 is a configuration for irradiating X-rays towards the subject P placed on the top 24 that interposed between the X-ray generator 22 and the X-ray detectors 23. The X-ray detector 23 detects the X-rays irradiated from the X-ray generator 22.

The diagnosis apparatus transferring mechanism 14 is a drive part for shifting and rotating the C arm 21. Moreover, the top transferring mechanism 15 is a drive for shifting the top 24. The diagnosis apparatus transferring mechanism 14 and the top transferring mechanism 15 operate based on control from the mechanism controller 13. Specifically, the mechanism controller 13 generates information indicating the direction, amount of movement, and speed of rotation and shifting of the C arm 21 and the X-ray detector 23 in accordance with control signals provided from the system controller 10. The system controller 10 is described later. The mechanism controller 13 outputs the generated information to the diagnosis apparatus transferring mechanism 14. Based on this information, the diagnosis apparatus transferring mechanism 14 shifts and rotates the C arm 21, thereby controlling the position and direction of the C arm 21.

Moreover, the mechanism controller 13 generates information indicating the direction, amount of movement, and speed of shifting the top 24 in accordance with the control signals from the system controller 10. The mechanism controller 13 outputs the generated information to the top transferring mechanism 15. Based on this information, the top transferring mechanism 15 controls the position of the top 24 by shifting the top 24 along the rostrocaudal direction of the subject P.

The X-ray generator 22 is configured by comprising an X-ray tube 221, a collimator 222, and an area dosimeter 223. The X-ray tube 221 accelerates electrons emitted from a filament using high voltage, generates X-rays by making the electrons collide with an anode target, and irradiates these X-rays outside from an irradiation window. As the material for the target, for example, Tungsten is used. The collimator 222 is arranged on the irradiation window of the X-ray tube 221, and is configured from a plurality of lead blades. The collimator 222 narrows down the irradiation field to a specified size in order not to expose unnecessary areas other than the observation area with X-rays irradiated from the X-ray tube 221. Moreover, a compensating filter M1 made from acrylic, and the like, which attenuates X-rays within a specified domain in the irradiation field only by a specified amount, may be provided on the emission side of the collimator 222 in order to prevent halation.

The area dosimeter 223 detects the dose of X-rays transmitted by the collimator 222. The area dosimeter 223 converts the dose of detected X-rays into electric charges, and outputs the electric charges to the distribution data generator 41 or the dose data generator 43 as output signals of an area dose. These output signals of the area dose are approximately proportionate to the irradiation intensity, irradiation area, and irradiation time of the X-rays. The distribution data generator 41 and the dose data generator 43 are described later. For example, by dividing the output signals of the area dosimeter 223 by the area of a standard position separate from the rotation center (that is, the isocentre) of the C arm 21 to the X-ray tube side only by a specific distance (hereinafter, may be referred to as the "dose calculation standard position"), the dose in the standard position (hereinafter, may be referred to as the "air kerma") is calculated. In other words, the output signals of the area dosimeter 223 are used to output signals indicating the irradiation intensity of the X-rays for each unit area in the dose calculation standard position as the air kerma.

The high voltage generator 12 generates a high voltage to apply between the anode and the cathode in order to accelerate thermo electrons generated from the cathode of the X-ray tube 221. The operation of the high voltage generator 12 is controlled by the X-ray controller 11. Specifically, based on this control information, the X-ray controller 11 receives control information indicating the X-ray irradiation condition from the system controller 10. The X-ray controller 11 generates information indicating the X-ray irradiation conditions configured from a tube current, tube voltage, X-ray pulse width, irradiation cycle (rate interval), fluoroscopic section, and the like, for operating the high voltage generator 12. Based on this information, the X-ray controller 11 controls the operation of the high voltage generator 12.

The X-ray detector 23 is configured from, for example, a flat panel detector (FPD: flat panel X-ray detector) comprising a plurality of detecting elements arranged in a matrix state. The X-ray detector 23 detects the intensity of X-rays, which are irradiated from the X-ray generator 22 in a specified irradiation field, for each detecting element. An X-ray grid that cuts scattered light of X-rays transmitted through a predetermined part of the subject P may be provided on the surface of the top 24 side of the FPD. The X-ray detector 23 converts the intensity of X-rays detected for each detecting element into electric signals, and outputs the signals to the distribution data generator 41 or image data generator 31 as image data. The distribution data generator 41 and the image data generator 31 are described later. Further, the X-ray detector 23 may be configured from a combination of an X-ray I.I. (Image Intensifier) and an X-ray TV camera instead of the FPD.

The image data generator 31 receives image data from the X-ray detector 23 and conducts image operations and image processing on this image data. For example, the image data generator 31 performs image operations for generating DSA (Digital Subtraction Angiography) image data, road map image data, long image data, and the like by subtraction between the image data before and after injecting a contrast agent. Moreover, the image data generator 31 conducts image processing such as contour extraction, smoothing, the tone collection, and the like, with respect to the image data obtained by image operations. Furthermore, the image data generator 31 receives the information indicating X-rays examination conditions related to this image data from the system controller 10. The image data generator 31 attaches the information indicating the X-ray examination conditions to the image data obtained by image operations and image processing, and outputs the image data to the display controller 32. Upon receiving the image data, the display controller 32 displays the X-ray image on the image display 332 based on the image data.

The system controller 10 configures a control center of the entire system, receives the X-ray irradiation conditions and conditions of the photographing position input by the operator as the X-ray examination conditions, and controls the operation of the X-ray controller 11 and the mechanism controller 13. Specifically, the system controller 10 generates control signals based on the irradiation conditions of X-rays input by the operator, and controls the operation of the X-ray controller 11 based on these control signals. Using these control signals, the X-ray controller 11 operates the high voltage generator 12 and irradiates X-rays from the X-ray generator 22. Moreover, the system controller 10 generates control signals based on the conditions of the photographing position input by the operator, and controls the operation of the mechanism controller 13 based on these control signals. By means of these control signals, the mechanism controller 13 operates the diagnosis apparatus transferring mechanism 14 and top transferring mechanism 15, and then controls the shifting as well as rotation of the C arm 21 and the shifting of the top 24.

Furthermore, the system controller 10 outputs information indicating the X-ray examination conditions to the distribution data generator 41, dose data generator 43, and image data generator 31. The distribution data generator 41 and dose data generator 43 are described later.

Figure 2:
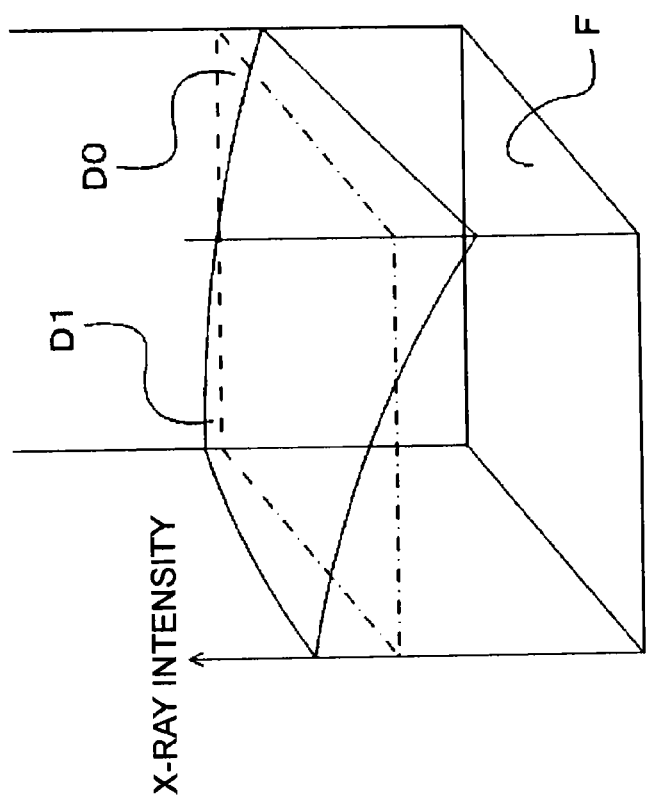
FIG. 2 illustrates an example of the distribution of the X-ray intensity within an irradiation field.

On the other hand, an X-ray examination apparatus related to the present embodiment has functions to manage the exposure dose of the subject P accompanying the X-ray irradiation based on the output signals of area dose from the area dosimeter 223. Here, the distribution of X-ray intensity within the X-ray irradiation field irradiated from the X-ray generator 22 is described with reference to FIG. 2. FIG. 2 illustrates an example of the X-ray intensity distribution within the irradiation field. D0 of FIG. 2 indicates an instance when the X-ray intensity distribution within the irradiation field is uniform. However, dispersion is caused in the X-ray intensity distribution within the irradiation field due to various reasons, and there are instances when the X-ray intensity distribution is not uniform, as shown D1. For example, when electrons emitted from a filament inside the X-ray tube 221 collide with a target, there is a tendency for the X-ray intensity to decrease towards the angle direction close to the anode surface due to the heel effect. Moreover, when the compensating filter M1 is used, the X-ray intensity decreases in the domain in which the compensating filter M1 is applied. Moreover, when the top 24 is interposed between the subject P and the X-ray generator 22, the X-ray transmits the top 24 and attenuates. Accordingly, the distribution data indicating the X-ray intensity distribution related to the present embodiment is prepared in advance, and during the X-ray examination, this distribution data is used to calculate the X-ray intensity for each domain within the irradiation field. Hereinafter, focusing on the function of managing the exposure dose, the composition of the operation of each process is described by dividing the processes into a "preparatory step" for generating distribution data and an "examination step" for calculating the entrance dose of X-rays.

(Preparatory Step)

The X-ray examination apparatus related to the present embodiment generates and stores in advance the distribution data indicating the X-ray intensity distribution for each X-ray irradiation condition, as a preparatory step prior to the X-ray examination. The method for generating this distribution data is described as follows, focusing on the configuration for generating the distribution data.

Generation of the distribution data is carried out unfixing the X-ray grid of the X-ray detector 23 detached and in a state without the top 24 and the compensating filter M1 interposing between the X-ray generator 22 and the X-ray detector 23. The system controller 10 receives the X-ray examination conditions input by the operator, generates control signals based on the conditions, and outputs the generated control signals to the X-ray controller 11 and the mechanism controller 13. By means of the X-ray controller 11 and the mechanism controller 13 operating based on these control signals, the C arm 21 operates and rotates such that the C arm 21 is placed at a predetermined photographing position, while X-rays are irradiated from the X-ray generator 22 towards a predetermined irradiation field determined based on the irradiation conditions of the X-rays. Moreover, the system controller 10 outputs the information indicating the X-ray examination conditions to the distribution data generator 41. Details on the distribution data generator 41 are described later.

The area dosimeter 223 detects the X-ray dose irradiated from the X-ray tube 221 and transmitted through the collimator 222. In the preparatory step, the area dosimeter 223 converts the dose of detected X-rays into electric charges and outputs the electric charges to the distribution data generator 41 as the output signals of the area dose. Moreover, whether the X-ray examination apparatus is operating as the "preparatory step" or "examination step" is recognized by, for example, the system controller 10 being operated by the operator.

Moreover, the X-ray detector 23 detects the intensity of X-rays irradiated from the X-ray generator 22 for each detecting element. The X-ray detector 23 converts the intensity of X-rays detected for each detecting element into electric signals, and outputs the signals to the distribution data generator 41 as image data.

The distribution data generator 41 receives the image data for each detecting element from the X-ray detector 23. The distribution data generator 41 divides the domain in which X-rays are detected as the image data (that is, the irradiation field) into a plurality of domains in advance. With the X-ray generator 22 as the standard, based on the distance to the X-ray detector 23 and the distance to the dose calculation standard position, the distribution data generator 41 converts each divided domain into a domain in the dose calculation standard position. Each of these domains in the dose calculation standard position is referred to as a "management unit domain." The distribution data generator 41 calculates SN ratio of X-rays for each of these management unit domains. Although the method for using the distribution data of the output from the X-ray detector 23 is simple, generally, outputs from the X-ray detector such as FPD are output after correcting the X-ray intensity distribution and dispersions in the sensitivity of the detector itself; therefore, application to the X-ray intensity distribution data is difficult. The method for calculating the SN ratio of X-rays for each of these management unit domains is described in detail in the following.

The distribution data generator 41 calculates a SD value (standard deviation) of the X-ray intensity based on the average X-ray intensity of each detecting element and the X-ray intensity dispersion for each of detecting element in each management unit domain. The distribution data generator 41 divides the average X-ray intensity by the calculated SD value, thereby calculating the ratio of the average X-ray intensity (output level) and the SD value of the management unit domain thereof as the SN ratio of X-rays in the management unit domain thereof. That is, the SD value of the calculated X-ray intensity corresponds to the noise part upon calculating this SN ratio.

Figure 3A:
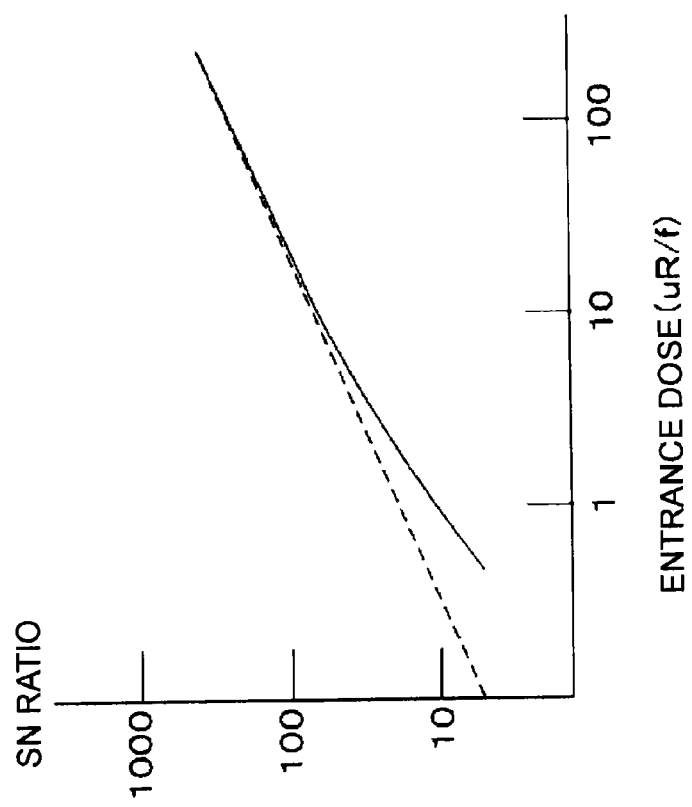
FIG. 3A is a graph illustrating a relation between the SN ratio of the X-ray intensity and an entrance dose.

On the other hand, the distribution data generator 41 measures in advance the relation between the SN ratio of X-rays and the entrance dose as a characteristic of the X-ray detector 23, and stores the characteristic as characteristic data. FIG. 3A is a graph showing the relation between the SN ratio of the X-ray intensity and the entrance dose as a characteristic of the X-ray detector 23, wherein, this characteristic is caused by X-ray quantum noise and unique noise of the X-ray detector 23. The generation and absorption of radiation including X-rays, and the like are a random phenomenon. Noise is accompanied because the frequency of generation and absorption of radiation follows the law of statistics. This noise corresponds to the X-ray quantum noise. Moreover, unique noise refers to unique noise of the X-ray detector 23, such as the noise of a circuit configuring the X-ray detector 23. As illustrated in FIG. 3A, nonlinearity is caused in domains with low doses. This is due to the effect of unique noise of the X-ray detector 23. On the other hand, when the dose is greater than a predetermined amount, the SN ratio of X-rays and the entrance dose become proportional. This is because when the intensity of X-rays increase and becomes greater than the predetermined dose, the effect of the unique noise of the X-ray detector 23 with respect to the X-ray quantum noise becomes small, and thereby negligible. Therefore, in this preparatory step, the distribution data generator 41 becomes capable of converting the SN ratio of X-rays into the entrance dose by means of setting the intensity of X-rays irradiated from the X-ray generator 22 such that the dose becomes greater than a predetermined value. According to such a configuration, the distribution data generator 41 converts the SN ratio calculated for each domain into the entrance dose of each domain based on these characteristic data. Moreover, these distributions may change depending on the X-ray tube voltage, thickness of the radiation quality filter, size of the irradiation field, and the like; therefore, data is accumulated under various conditions.

Figures 3B, 4A:
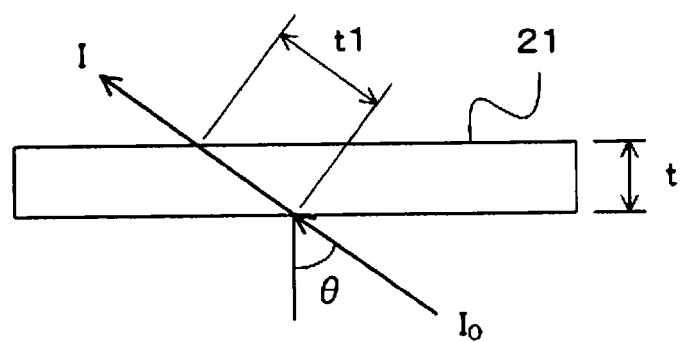
FIG. 3B is a figure describing distribution data.
FIG. 4A is a figure describing a relation between a top and the entrance dose.

Further, the distribution data generator 41 generates distribution data showing the distribution of the X-ray intensity under various conditions. The distribution data generator 41 comprises the distribution data for each management unit domain in the dose calculation standard position. For example, the example of FIG. 3B illustrates the dose ratio (%) of each management unit domain when the dose obtained by dividing the entire area dose by the entire irradiation area (that is, the air kerma) is "100" (the dose at this case may be referred to as the "average dose"). For example, a domain "a3" indicates "60." "60" indicates that the dose is 60% of the average dose. Furthermore, a domain "c2" indicates "125." "125" indicates that the dose is 125% of the average dose. That is, in FIG. 3B, the ratio is corrected such that the overall average becomes "100."

The distribution data generator 41 receives information indicating the X-ray examination conditions upon generation of the distribution data from the system controller 10. The distribution data generator 41 associates the generated distribution data with the information indicating the X-ray examination conditions, and stores the distribution data in the distribution data storage 42. The distribution data storage 42 is a storage domain for storing distribution data. The distribution data storage 42 is configured to allow reading of the distribution data corresponding to the X-ray examination conditions by specifying the X-ray examination conditions. As described above, the distribution data generator 41 generates the distribution data for each X-ray examination condition, and stores the generated distribution data in the distribution data storage 42.

(Examination Step)

Next, the "examination step" for calculating the entrance dose of X-rays is described. The X-ray examination apparatus related to the present embodiment irradiates X-rays towards the subject P, and calculates the entrance dose for each domain based on the area dose detected by the area dosimeter 223 along with the distribution data corresponding to the X-ray examination conditions at the time. Hereinafter, descriptions are provided focusing on the configuration operated as above.

When the X-ray examination conditions are set by the operator, the system controller 10 generates control signals based on these conditions, and outputs the signals to the X-ray controller 11 and the mechanism controller 13. Thereby, the C arm 21 operates and rotates so that the C arm 21 is placed at the predetermined photographing position. Along with the shifting of the top 24, X-rays are irradiated from the X-ray generator 22 towards the subject P on the top 24, based on the X-ray irradiation conditions. The system controller 10 outputs information indicating these X-ray examination conditions to the image data generator 31 and dose data generator 43. Details on the dose data generator 43 are described later.

The X-ray detector 23 detects the intensity of X-rays irradiated from the X-ray generator 22 for each detecting element. The X-ray detector 23 converts the intensity of X-rays detected for each detecting element into electric signals, and outputs the signals to the image data generator 31 as image data. The image data generator 31 carries out image operations and image processing on the image data, attaches the information indicating the X-ray examination conditions received from the system controller 10 to the image data, and outputs the image data on the display controller 32.

The area dosimeter 223 detects the X-ray dose irradiated from the X-ray tube 221 and transmitted through the collimator 222. The area dosimeter 223 converts the dose of detected X-rays into electrical charges, and outputs the electrical charges to the dose data generator 43 as the output signals of the area dose.

The dose data generator 43 receives the information indicating the conditions of the X examination from the system controller 10. The dose data generator 43 extracts the distribution data associated with the information from the distribution data storage 42.

Further, the dose data generator 43 receives the output signals of the area dose from the area dosimeter 223. The area dose indicated by these output signals corresponds to the entire area dose. The dose data generator 43 calculates the entrance dose for each domain in the dose calculation standard position, based on the entire area dose and the dose ratio for each domain included in the distribution data. For example, an assumption is made such that the dose obtained by dividing the output signals from the area dosimeter 223 by the irradiation area of the entire dose calculation standard position is 100 mGy, and the distribution data illustrated in FIG. 3B is extracted. In this case, for example, the ratio associated with a domain "b2" is "100"; therefore, the entrance dose of the domain "b2" becomes 100 mGy× 100%=100 mGy. Moreover, the ratio associated with a domain "b4" is "110"; therefore, the entrance dose of the domain "b4" becomes 100 mGy×110%=110 mGy.

Next, the dose data generator 43 calculates the domain at which X-rays attenuate along with use of the compensating filter M1 and the transmission through the top 24 as well as the amount of attenuation thereof based on the information indicating the X-ray examination conditions. As an example, a method for calculating the amount of X-ray attenuation by means of transmitting through the top 24 when the top 24 is interposed between the subject P and the X-ray generator 22 is described with reference to FIG. 4A. FIG. 4A illustrates an instance when X-rays of an entrance dose $I_0$ are incoming at an incidence angle θ with respect to the top 24 of thickness t. First, the dose data generator 43 specifies the domain, at which the top 24 is interposed between the subject P and the X-ray generator 22 within the X-ray irradiation field, from the information indicating the X-ray examination conditions. Next, the dose data generator 43 calculates the amount of X-ray attenuation within the specified domain. The X-ray attenuation (entrance dose) following transmission through the top 24 is calculated based on a distance t1 at which the X-rays transmit through the top 24, an absorbing coefficient u of the X-rays of the top 24, and the entrance dose $I_0$.

The distance t1 at which X-rays transmit through the top 24 is calculated using the following formula.

$$t1 = t/\cos \theta$$

Moreover, the entrance dose I of the X-rays that have transmitted through the top 24 is calculated using the following formula.

$$I = I_0 \exp(-u \cdot t1)$$

When using the compensating filter M1, the method for calculating the attenuation is different from when the top 24 is interposed. This is because the X-rays that have transmitted through the compensating filter M1 are detected by the area dosimeter 223. The case of using the compensating filter M1 is explained with reference to FIGS. 4B to 4D. FIGS. 4B to 4D illustrate the relation between the compensating filter M1 and the entrance dose. As in FIG. 4B, a description is provided with some of the compensating filter M1 inside. In order to correct the effects of the compensating filter M1, there are some cases such a method for correcting the distribution data of the X-ray intensity, and a method for correcting the dose calculation result at the dose calculation standard position. Here, the former is explained. Assume that the transmittance of the compensating filter M1 is A×100%. Also, assume that the ratio of the area in which the compensating filter M1 is inserted is B×100% with respect to the entire area dosimeter 223. In the distribution data of X-ray intensity such as that illustrated in FIG. 3B, the X-ray intensity attenuates to the ratio of A in the domain with the compensating filter M1 inserted. For example, FIG. 4B illustrates the distribution of the attenuation rate of the X-ray intensity when 40% of the entire area dosimeter 223 is covered with the compensating filter M1 having transmittance of 50% (A=0.5). The converted distribution data is prepared and stored in advance such that the average becomes 100 (that is, 100%) based on the distribution illustrated in FIG. 4B. The detailed method for preparing this distribution data is described in the following with the case of FIG. 4B as an example.

First, a sum (D1) of the value corresponding to each domain when the value of each domain is 100 and a sum (D2) of the value corresponding to each domain when the compensating filter M1 is applied are calculated. In the present embodiment, the domains are divided into 5×5; therefore, it becomes D1=5×5×100=2500. Moreover, domains d1 to d5 and e1 to e5 are attenuated to 50 using the compensating filter M1; therefore, the D2 becomes D2=100×15+50×10=2000. A coefficient D1/D2 is calculated based on those calculated D1 and D2. In the case of the example in FIG. 4B, the D1/D2 becomes D1/D2=2500/2000=1.25. The distribution illustrated in FIG. 4B is corrected by the calculated coefficient D1/D2; thereby, distribution data converted to have an average of 100 is prepared. FIG. 4C illustrates the distribution data in which the distribution illustrated in FIG. 4B is prepared by correcting using the coefficient D1/D2. As illustrated in FIG. 4C, domains a1 to a5, b1 to b5, and c1 to c5 are corrected to 125, while the domains d1 to d5 and e1 to e5 are corrected to 62.5.

In the case such that the compensating filter M1 is being used, when the entrance dose for each domain is calculated, the dose data generator 43 corrects the distribution data, which is obtained by multiplying the value of the distribution data extracted based on the information indicating the X-ray examination conditions by the value of the distribution data prepared based on the conditions of the compensating filter M1 for each domain. The corrected distribution data configured by correcting the distribution data illustrated in FIG. 3B based on the distribution data illustrated in FIG. 4C is illustrated in 4D. The domain M2 in FIG. 4D corresponds to the area in which the compensating filter M1 is applied. For example, the domain a1 indicates "90"% in FIG. 3B, so the domain a1 is not covered by the compensating filter M1. Therefore, by multiplying the value "125"% corresponding to the domain a1 of the distribution data illustrated in FIG. 4C by the value "90"%, a value following correction becomes "112.5"%. Moreover, the domain d1 indicates "100"% in FIG. 3B, so the domain d1 is covered by the compensating filter M1. Accordingly, a value following correction becomes "62.5"% by multiplying the value "62.5"% corresponding to the domain d1 of the distribution data illustrated in FIG. 4C by the value "100"%. The dose data generator 43 should calculate the amount of X-ray attenuation from the corrected distribution data following correction of the distribution data.

That is, the dose data generator 43 corrects the entrance dose calculated for each domain based on the calculated amount of attenuation.

Figure 5A:
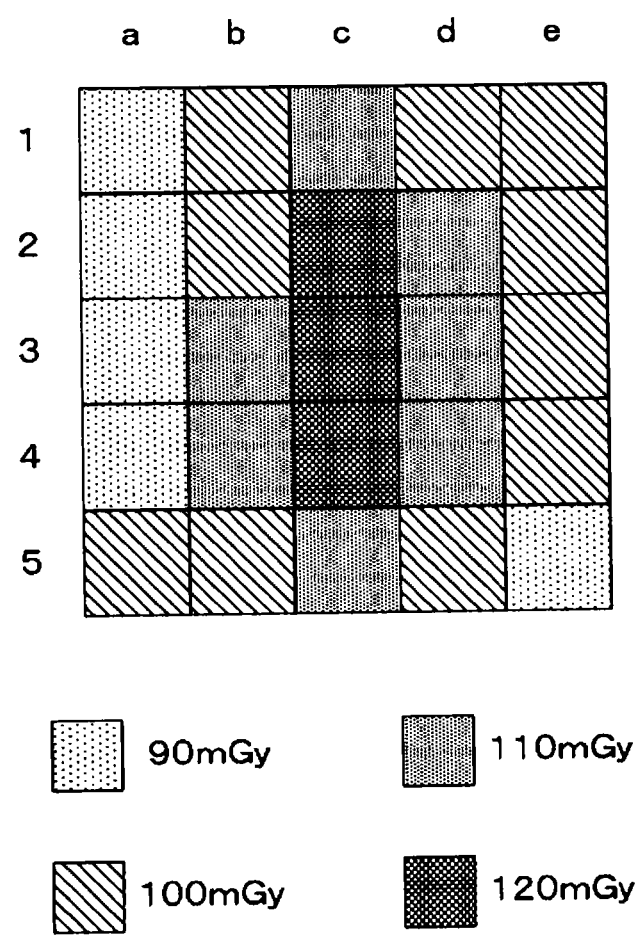
FIG. 5A illustrates an example of a method for managing the entrance dose.

As described above, the dose data generator 43 calculates the entrance dose for each domain, and generates the dose data associated with the domain, which is the source for calculation of the entrance dose thereof. For example, FIG. 5A schematically illustrates an example of the dose data according to the present embodiment. In addition, FIG. 5B indicates the conventional method in which consideration is not given to the X-ray intensity distribution of the irradiation field. For example, in the example illustrated in FIG. 5A, the entrance dose "100 mGy" is associated with the domain "b1," Further, the entrance dose "120 mGy" is associated with the domain "c3." Furthermore, in the example illustrated in FIG. 5B, the average entrance dose "100 mGy" is associated with the entire irradiation field. In this manner, by means of using the distribution data, it becomes possible to divide the irradiation field into a plurality of domains and calculate the entrance dose for each domain thereof. The dose data generator 43 outputs the generated dose data to the display controller 32. The dose data generator 43 may also associate the generated dose data with the information indicating the X-ray examination conditions, and store the data in the dose data storage 44. The dose data storage 44 is a storage domain for storing the dose data. The dose data storage 44 is configured to specify the X-ray examination conditions, and allow reading of the dose data corresponding to the specified conditions.

The display controller 32 receives the information indicating the position and angle of the C arm 21, the position of the top 24, the position of the X-ray detector 23, the size of the irradiation field, and the states of the collimator 222 from the system controller 10. The display controller 32 calculates the X-ray irradiation position and size of the irradiation field for a modeled patient (hereinafter, referred to as a "patient model") based on those information above. Further, the display controller 32 receives the dose data in which the entrance dose for each domain is calculated based on the distribution data from the dose data generator 43. The display controller 32 distinguishably displays the entrance dose on the irradiation surface of the patient model in the domain unit (for example, by color-coding in accordance with the entrance dose) on the dose information display 331. Furthermore, this dose data may be, for example, calculated as an integral dose in real time during examination, and successively displayed on the dose information display 331.

Figure 6A:
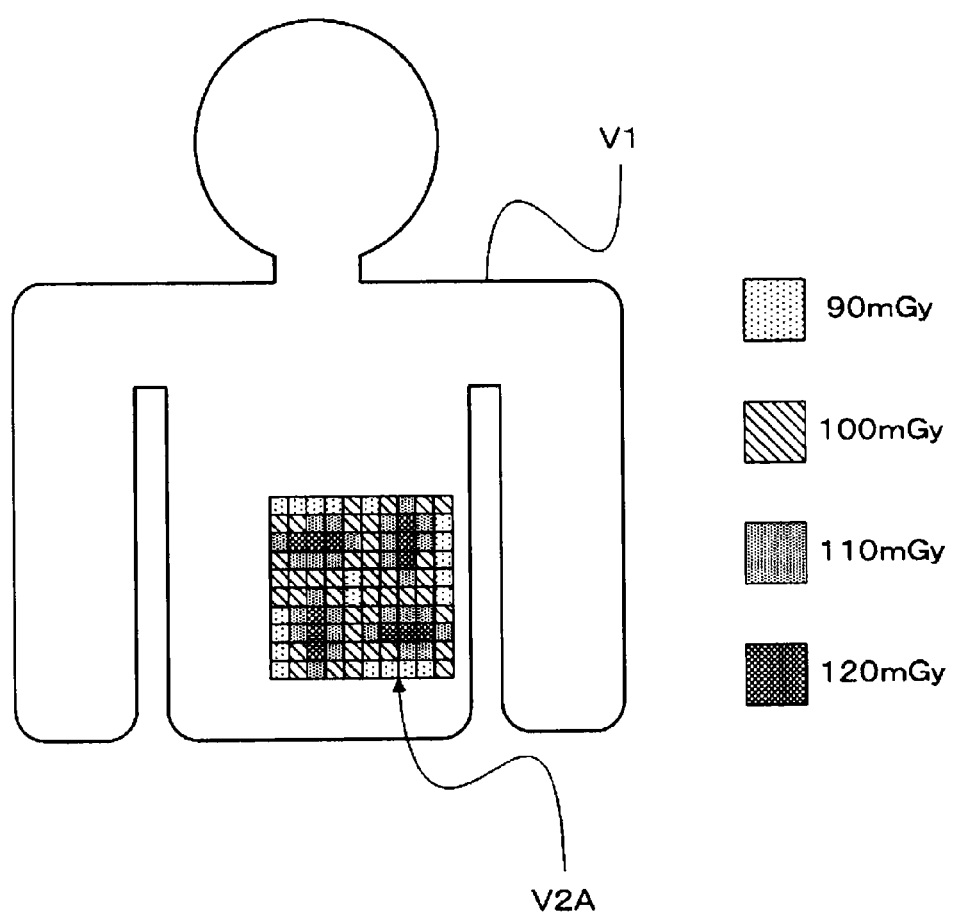
FIG. 6A is an example of display modes of information indicating the entrance dose.

FIG. 6A illustrates a case in which the entrance dose of each domain is distinguishably displayed on the patient model as an example of display modes of the information indicating the entrance dose. Further, the display controller 32 may extract the dose data corresponding to the information received from the system controller 10 from the dose data storage 44, and display the extracted data on the dose information display 331. By means of operating in this manner, the dose data may be collected in advance and displayed on the dose information display 331 later for use in diagnosis.

Further, the dose data generator 43 may receive image data from the image data generator 31, associate this image data with the generated dose data, and store the associated data in the dose data storage 44. In this case, the display controller 32 reads the image data and dose data from the dose data storage 44, and displays the X-ray image and entrance dose on the dose information display 331 based on this image data and dose data. The image data and dose data are associated and stored in the above configuration; therefore, for example, it is possible to operate with a mode such that preliminarily photographing the X-ray image and generating the dose data, displaying the X-ray image and the entrance dose on the dose information display 331 later.

(Process)

Figure 7A:
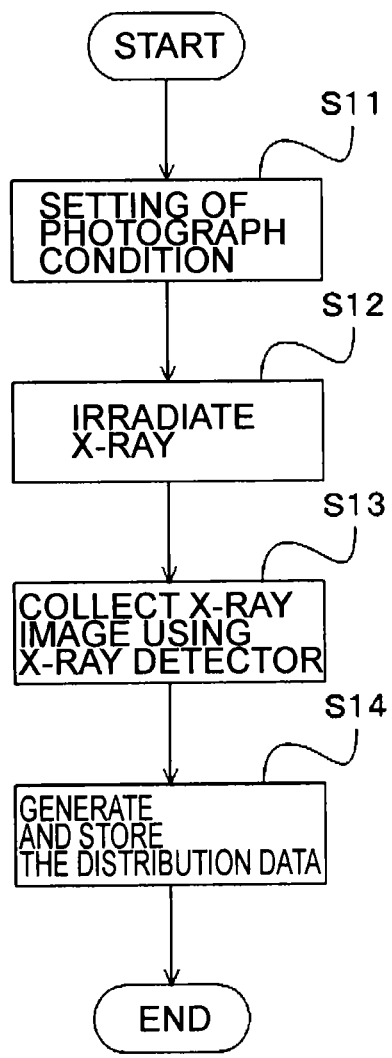
FIG. 7A is a flow chart illustrating a flow of processes related to generation of the distribution data.

Next, a series of operations of the X-ray diagnosis apparatus related to the present embodiment is described. First, the operation of a preparatory step for preliminarily generating and storing the distribution data for each X-ray irradiation condition is described with reference to FIG. 7A. FIG. 7A is a flowchart illustrating the series of operations of the preparatory step.

(Step S11)

The distribution data is generated by removing the X-ray grid of the X-ray detector 23 under a state in which the top 24 and compensating filter M1 do not interpose between the X-ray generator 22 and the X-ray detector 23. Moreover, functions such as image processing, and the like are shut OFF so that the irradiated X-rays and outputs from the X-ray detector 23 become proportionate. The system controller 10 receives the X-ray examination conditions input by the operator, generates control signals based on the X-ray examination conditions, and outputs the generated control signals to the X-ray controller 11 and mechanism controller 13. Moreover, the system controller 10 also outputs the information indicating these X-ray examination conditions to the distribution data generator 41.

(Step S12)

The mechanism controller 13 controls the diagnosis apparatus transferring mechanism 14 based on control signals from the system controller 10, and operates as well as rotates the C arm 21 in order to place the C arm 21 at the photographing position instructed as the X-ray examination condition. Moreover, the X-ray controller 11 controls the high voltage generator 12 based on the control signals from the system controller 10, and makes the X-ray generator 22 irradiate X-rays based on the X-ray irradiation condition instructed as the X-ray examination condition.

(Step S13)

Further, the X-ray detector 23 detects the intensity of X-rays irradiated from the X-ray generator 22 for each detecting element. The X-ray detector 23 converts the intensity of the X-rays detected for each detecting element to electric signals, and then outputs the signals to the distribution data generator 41 as image data.

(Step S14)

The distribution data generator 41 receives the image data for each detecting element from the X-ray detector 23. The distribution data generator 41 divides the domain at which X-rays were detected as the image data (that is, the irradiation field) into a plurality of domains in advance, and then calculates the SN ratio of the image data for each of these domains. Specifically, the distribution data generator 41 calculates the SD value (standard deviation) of the X-ray intensity based on the average X-ray intensity for each detecting element and the X-ray intensity dispersion in each detecting element regarding each domain. The distribution data generator 41 also divides the average X-ray intensity by the calculated SD value, thereby calculating the ratio of the SD value for the average X-ray intensity of the domain thereof (output level) as the SN ratio of X-rays in the domain thereof.

Meanwhile, the distribution data generator 41 preliminarily measures the relation between the SN ratio of the X-rays and the entrance dose as a characteristic of the X-ray detector 23, and stores this as characteristic data. The distribution data generator 41 converts the SN ratio calculated for each domain into the entrance dose for each domain based on this characteristic data. The distribution data generator 41 then converts the entrance dose of each of these domains into the ratio for each of these domains (refer to FIG. 3B) such that the average value becomes uniform.

The distribution data generator 41 receives the information indicating the X-ray examination conditions upon generating the distribution data from the system controller 10. The distribution data generator 41 then associates the generated distribution data with the information indicating the X-ray examination conditions, and stores the associated data in the distribution data storage 42. In this manner, the distribution data generator 41 generates distribution data for each X-ray examination condition, and stores the generated distribution data in the distribution data storage 42.

Figure 7B:
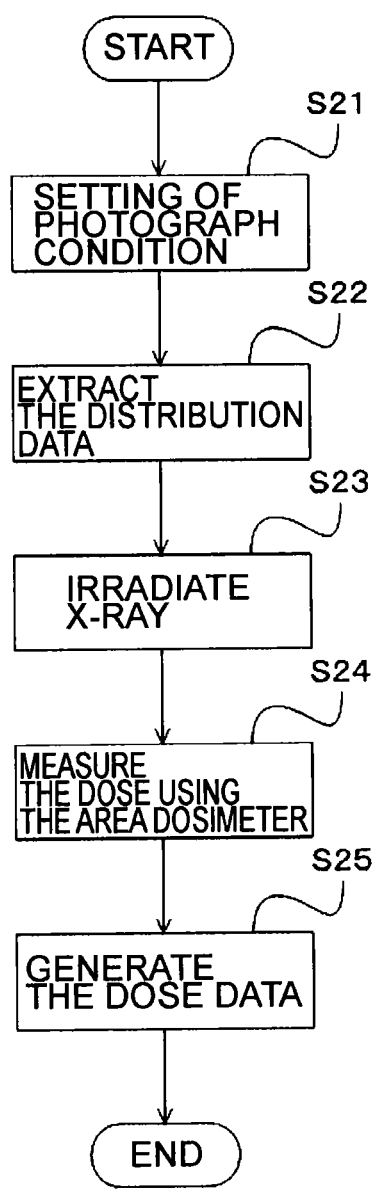
FIG. 7B is a flow chart illustrating a flow of processes related to calculation of the entrance dose.

Next, the examination step of irradiating X-rays onto the subject P, generating X-ray images, and calculating the entrance dose of X-rays is explained with reference to FIG. 7B. FIG. 7B is a flow chart illustrating a series of operations of the examination step.

(Step S21)

When the X-ray examination conditions are set by the operator, the system controller 10 generates control signals based on these conditions, and outputs the signals to the X-ray controller 11 and mechanism controller 13. The system controller 10 also outputs the information indicating these X-ray examination conditions to the image data generator 31 and dose data generator 43.

(Step S22)

The dose data generator 43 receives the information indicating the X-ray examination conditions from the system controller 10. The dose data generator 43 then extracts the distribution data associated with this information from the distribution data storage 42.

(Step S23)

The mechanism controller 13 controls the diagnosis apparatus transferring mechanism 14 and the top transferring mechanism 15 based on control signals from the system controller 10, and operates and rotates the C arm 21 in order to place the C arm 21 at the photographing position instructed as the X-ray examination condition, as well as shifting the top 24. Moreover, the X-ray controller 11 controls the high voltage generator 12 based on the control signals from the system controller 10, and makes the X-ray generator 22 irradiate X-rays based on the X-ray irradiation condition instructed as the X-ray examination condition. Thereby, X-rays are irradiated from the X-ray generator 22 towards the subject P on the top 24.

(Step S24)

The area dosimeter 223 detects the dose of X-rays emitted from the X-ray tube 221 and transmitted through the collimator 222. The area dosimeter 223 then converts the dose of detected X-rays into electric charges and outputs the electric charges to the dose data generator 43 as the output signals of the area dose.

(Step S25)

The dose data generator 43 receives the output signals of the area dose from the area dosimeter 223. The area dose indicated by these output signals corresponds to the entire area dose. The dose data generator 43 then calculates the entrance dose for each domain based on the ratio of the entire area dose and the dose for each domain included in the distribution data.

Next, the dose data generator 43 calculates the domain at which X-rays attenuate along with the use of the compensating filter M1 and the transmission through the top 24 as well as the amount of attenuation thereof, based on the information indicating the X-ray examination conditions. The dose data generator 43 then corrects the entrance dose calculated for each domain, based on the calculated amount of attenuation.

The dose data generator 43 calculates the entrance dose for each domain, and generates the dose data associated with the domain, which is the source for calculation of the entrance dose thereof. The dose data generator 43 then outputs the generated dose data onto the display controller 32.

The display controller 32 receives the information indicating the position and angle of the C arm 21, the position of the top 24, the position of the X-ray detector 23, the size of the irradiation field, and the state of the collimator 222 from the system controller 10. The display controller 32 calculates the X-ray entrance position and the size of the irradiation field with respect to the patient model based on the information above. Further, the display controller 32 receives the dose data, in which the entrance dose for each domain is calculated based on the distribution data, from the dose data generator 43. The display controller 32 distinguishably displays the entrance dose on the irradiation surface of the patient model in the domain unit on the dose information display 331. In this manner, according to the X-ray examination apparatus related to the present embodiment, the irradiation field may be divided into a plurality of domains and the entrance dose for each domain thereof may be calculated by using the distribution data.

Here, FIG. 5B is referred. FIG. 5B is a figure schematically illustrating an example of a case that the dose data is generated without using the distribution data. The dose data generator 43 recognizes the X-ray intensity dispersion within the irradiation field based on the distribution data. Therefore, for example, when the distribution data is not used as in the conventional method, it was difficult to calculate the entrance dose for each domain by recognizing each domain, as illustrated in FIG. 5B. For example, FIG. 6B illustrates an example of displayed modes of the information indicating the entrance dose under this condition. In this manner, when the distribution data is not used, the entrance dose has been managed under the assumption that X-rays are being uniformly irradiated within the irradiation domain, as illustrated in FIG. 5B and V2B of FIG. 6B.

In contrast, according to the X-ray examination apparatus of the present embodiment, the irradiation field may be divided into a plurality of domains and the entrance dose may be calculated for each domain by using the distribution data. Thereby, for example, as illustrated in FIG. 5A and FIG. 6A, even when the distribution of the X-ray intensity is varied and the entrance dose of the X-ray locally increases, the X-rays may be detected and managed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

DESCRIPTION OF SYMBOLS

10 system controller
11 X-ray controller
12 high voltage generator
13 mechanism controller
14 diagnosis apparatus transferring mechanism
15 top transferring mechanism
20 capturing unit
21 C arm
22 X-ray generator
221 X-ray tube
222 collimator
223 area dosimeter
23 X-ray detector
24 top
31 image data generator
32 display controller
331 dose information display
332 image display
41 distribution data generator
42 distribution data storage
43 dose data generator
44 dose data storage

The invention claimed is:

1. An X-ray diagnosis apparatus comprising
an X-ray source configured to irradiate X-rays toward a desired irradiation field;
an X-ray detector configured to detect the intensity of the X-rays irradiated by the X-ray source;
an image data generator configured to generate an X-ray image based on the intensity of the X-rays detected by the X-ray detector;
an area dosimeter interposed between the X-ray source and the X-ray detector, and configured to detect an area dose of the X-rays irradiated by the X-ray source;
an intensity distribution data generator configured to generate distribution data, showing dose ratio for each of a plurality of subdomains of an irradiation field by using distribution data indicating SN ratio of the X-rays for each of the plurality of subdomains based on the intensity of the X-rays detected by the X-ray detector, as intensity distribution data showing the intensity for each of the plurality of subdomains; and
a dose distribution data generator configured to generate dose distribution data showing the dose of the X-rays for each of the plurality of subdomains, based on the intensity distribution data generated by the intensity distribution data generator and the area dose detected by the area dosimeter.

2. The X-ray diagnosis apparatus according to claim 1, wherein
each of the plurality of subdomains is converted into a management unit domain based on a distance from the X-ray source to the X-ray detector and a distance from the X-ray source to a dose calculation standard position.

3. The X-ray diagnosis apparatus according to claim 1, comprising
an intervention interposed between the X-ray source and the X-ray detector; wherein
the dose distribution data generator calculates attenuation of the X-rays due to the intervention and corrects the dose distribution data by using the attenuation of the X-rays.

4. The X-ray diagnosis apparatus according to claim 3, wherein
the area dosimeter is configured to detect directly the area dose of the X-rays irradiated by the X-ray source.

5. The X-ray diagnosis apparatus according to claim 3, wherein
the X-ray detector is configured to detect the X-rays irradiated by the X-ray source and transmitted through the intervention.

6. The X-ray diagnosis apparatus according to claim 1, wherein
the intensity distribution data generator is configured to generate distribution data showing the dose for each of the plurality of subdomains from the distribution data indicating the SN ratio of the X-rays for each of the plurality of subdomains by using characteristic data indicating a relation between the SN ratio and the dose of the X-rays, and generate distribution data showing the dose ratio for each of the plurality of subdomains by using the distribution data showing the dose for each of the plurality of subdomains.

7. The X-ray diagnosis apparatus according to claim 1, comprising
a display controller configured to display each dose of the plurality of subdomains on a part corresponding to each of the plurality of subdomains in the X-ray image, based on the dose distribution data generated by the dose distribution data generator.

8. A dose distribution data generation method in an X-ray diagnosis apparatus configured to detect X-rays output from a X-ray source and transmitted through a subject, and generate images of the inside of the subject, the dose distribution data generation method comprising;
detecting the intensity of the X-rays output from the X-ray source,
generating distribution data, showing dose ratio for each of a plurality of subdomains of an irradiation field by using distribution data indicating SN ratio of the X-rays for each of the plurality of subdomains based on the detected intensity of the X-rays, as intensity distribution data showing the intensity of X-rays for each of the plurality of subdomains,
detecting an area dose of the X-rays output from the X-ray source, and
generating dose distribution data showing the dose of the X-rays for each of the plurality of subdomains based on the generated intensity distribution data and the detected area dose.

* * * * *